United States Patent [19]

Devidas et al.

[11] Patent Number: 5,030,450

[45] Date of Patent: Jul. 9, 1991

[54] METHOD FOR INHIBITING NEMATODE INFECTION OF PLANTS WITH NEMATOSTATIC TRICHOTHECENE COMPOSITIONS

[75] Inventors: Premachandran Devidas, Grayslake; Ronald R. Rasmussen, Waukegan, both of Ill.

[73] Assignee: Abbott Laboratories, Abbott Park, Ill.

[21] Appl. No.: 442,287

[22] Filed: Nov. 28, 1989

[51] Int. Cl.[5] ...................... A01N 65/00; A01N 63/00

[52] U.S. Cl. ............................ 424/195.1; 424/85.91; 424/93

[58] Field of Search ...................... 424/195.1, 93, 122, 424/85.91

[56] References Cited

U.S. PATENT DOCUMENTS

| | | | |
|---|---|---|---|
| 3,087,859 | 4/1963 | Smythe et al. | 424/122 |
| 4,744,981 | 5/1988 | Pavanasasivam | 424/85.91 |
| 4,764,372 | 8/1988 | Herrnstadt et al. | 424/93 |

FOREIGN PATENT DOCUMENTS

| | | |
|---|---|---|
| 3295863 | 1/1965 | Australia . |
| 3326263 | 1/1965 | Australia . |
| 0282057 | 9/1988 | European Pat. Off. . |
| 421387 | 2/1963 | Netherlands . |

OTHER PUBLICATIONS

W. Loeffler et al., Pharmaceuticals 30 (1964).

Yoshio Ueno et al., J. Biochm., vol. 74, pp. 285-296.

Cutler, American Chem. Soc./Biotech 4, pp. 50-72.

McDougal, Progress in Chemistry of Organic Nat. 47, pp. 153,

Radzhabava, Dokl. Akad. Nauk, Azerb SSR 27(5) pp. 58-60.

*Primary Examiner*—Stanley J. Friedman

*Assistant Examiner*—Kevin E. Weddington

*Attorney, Agent, or Firm*—Steven F. Weinstock

[57] ABSTRACT

New trichothecene compositions are disclosed along with their use in methods of inhibiting nematode infection of plants.

7 Claims, No Drawings

METHOD FOR INHIBITING NEMATODE INFECTION OF PLANTS WITH NEMATOSTATIC TRICHOTHECENE COMPOSITIONS

FIELD OF THE INVENTION

The present invention relates to compounds and methods of inhibiting nematode infection of plants.

BACKGROUND OF THE INVENTION

Plant parasitic nematodes cause serious economic damage to many agricultural crops around the world. These nematodes are microscopic worms and are, in general, obligate parasites of plants. They feed mostly on the roots of host plants; however, several genera are known to parasitize above-ground parts including stem, leaves and flowers as well. Almost all the major plant species are susceptible to infection by species of nematodes (notable exceptions are in the marigolds and asparagus). For example, one of the most important genera of plant nematodes, root-knot nematodes, (*Meloidogyne* species (spp.)) is capable of parasitizing more than 3,000 species of crop plants. These plants include agronomic crops, vegetables, fruits, flowering trees and shrubs. Nematodes reportedly cause crop loss equivalent to 6 billion dollars in the United States alone and more than 100 billion dollars around the world.

The symptoms due to phytoparasitic nematode injury vary widely depending on the plant host, the nematode species, age of the plant, geographical location, climatic conditions, etc. In general, an overall patchy appearance of plants in a field is considered indicative of nematode injury. More specifically, nematode injury results in galling of the roots (abnormal swelling in the tissues due to rapid multiplication of cells in the cortical region) caused by species of root-knot (*Meloidogyne* spp.) and cyst (*Heterodera* spp.) nematodes, lesions (localized, discolored area) caused by lesion nematodes (*Pratylenchus* spp.), suppression of cell division resulting in "stubby" roots (*Trichodorus* spp.), growth abnormalities including crinkling or twisting of aboveground parts (*Aphelenchoides* spp.) and even cell necrosis (death) in some cases. Plant parasitic nematodes may be endoparasitic in nature as in the case of the root-knot and lesion nematodes, or ectoparasitic as in the dagger nematode (*Xiphinema* spp.) and lance nematode (*Hoplolaimus* spp.). Nematodes can be vectors of plant viruses and are also known to induce disease complexes by facilitating the entry of other plant pathogenic fungi and bacteria.

Chemical nematocides as soil fumigants or nonfumigants have been in use for many years and represent one of the few feasible processes for countering nematodes. At present, the process involves repeated applications of synthetic chemicals to the ground prior to planting the crop. These chemicals are extremely toxic to organisms other than nematodes and pose a serious threat to the environment. With the renewed emphasis on clean water and air by the United States Environmental Protection Agency (EPA), and the detection of many of these active ingredients or the metabolites thereof in ground water and in several non-target organisms, there has been serious concern about the manufacture and/or use of these chemicals. One of the most effective, economical and widely used nematocides, DBCP (1,2-dibromo-3-chloropropane), was judged to induce male sterility and possible carcinogenesis and was reported in ground water. Another widely used chemical, EDB (ethylene dibromide), was also found in ground water. Yet another very common insecticide-nematocide, aldicarb (2-methyl-2-(methylthio)propionaldehyde-O-(methylcarbamoyl)oxime), was found to be acutely toxic and was found in ground water in several regions of the United States. Carbofuran (2,3-dihydro-2,2-dimethyl-7-benzofuranyl methylcarbamate) and 1,3-D (1,3-dichloropropane), two commonly used nematocides, are under special review by the EPA, because of their avian toxicity and possible carcinogenic effects.

Trichothecenes are a group of closely related sesquiterpenoids that are produced by various species of fungi. Illustrative genera of fungi that produce trichothecenes are *Fusarium*, *Cephalosporium*, *Myrothecium*, *Trichothecium*, *Trichoderma*, *Cyclindiocarpon*, *Stachybotrys*, *Verticimonosporium*, *Calonectria*, and *Arthrobotrys*.

Several trichothecenes are well-known and commercially available, such as from Sigma Chemical Co., St. Louis, MO. Illustrative trichothecenes include verrucarin A, verrucarol, HT-2 toxin, T-2 toxin, diacetoxyscirpenol, roridin A, acetyl T-2 toxin, neosolaniol, tetracetyl T-2 toxin, T-2 tetraol, T-2 triol, diacetylnivalenol and crotocin.

The structures of the trichothecenes contain a ring system named trichothecane. Godtfredsen et al., Helv. Chim. Acta, 174:1666 (1967). All naturally occurring trichothecene toxins contain an olefinic bond at C-9,10 and most have an epoxy group at C-12,13. Naturally occurring trichothecenes may be classified into five groups (A-E) according to their chemical characteristics.

The trichothecenes of group A possess a hydroxy or an acyloxyl group at C-4 and may have these groups at C-3, C-7, C-8 and C-15, and include HT-2 toxin, T-2 toxin, verrucarol and acetyl T-2 toxin.

The trichothecenes of group B possess a carbonyl group at C-8, and include nivalenol, diacetylnivalenol an trichothecin.

The trichothecenes of group C are macrocyclic trichothecenes and include verrucarin A and roridin A.

The only trichothecene of group D is crotocin which possesses a second epoxide group at C-7,8.

The trichothecenes of group E are trichoverroids which possess either partial or complete carbon chains at C-4 and C-15.

The trichothecenes are stable in the solid state. At extreme pH's, however, the compounds undergo reaction in solution. The esters are saponified by treatment with alkali and the C-12,13-epoxide group is opened by strong mineral acid. Hydrogenation of the C-9,10 double bond results in a slight decrease in toxicity of the compounds, and opening of the C-12,13 epoxide group alters biological activity.

Trichothecenes are known to possess antifungal, antibacterial, antiviral, insecticidal and phytotoxic activity. McDougal et al. (1985) in *Progress in the Chemistry of Organic Natural Products* (Herz et al., eds. Springer-Verlag, NY) p. 153–219. The trichothecenes have been shown to be toxic to plants at concentrations as low as $10^{-7}$ molar (M), and extremely toxic at concentrations above about $10^{-5}$ M. Cutler (1988) in *Biotechnol. for Crop Protect.* (Am. Chem. Soc.) p. 50–72.

The nematocidal activity of phytotoxic concentrations of a simple trichothecin (20–500 micrograms (ug) per milliliter (ml)) has been reported by Radzhabova (1971) Dokl. Akad. Nauk. Azerb. SSR, 27:58–60. The trichothecin solution utilized was directly applied to free-living nematodes (*Turbatrix aceti*) on microscope slides. The trichothecin solutions were prepared in 5% ethanol and a 5% ethanol solution was used as a control. Radzhabova reports that the time period necessary to produce a killing of 50% of the nematodes tested ($LD_{50}$) is significantly reduced as the trichothecin concentration increases. A solution having 500 ug/ml trichothecin produced an $LD_{50}$ about 4-fold lower than that for a 62.5 ug/ml trichothecin solution and an $LD_{50}$ approximately one-half that produced by a 250 ug/ml trichothecin solution in the assay. Since it is known that many species of nematodes are susceptible to ethanol, this article does not teach that trichothecenes are nematocidal and in no way discloses the nematostatic activity of trichothecenes that is part of the present invention.

SUMMARY OF THE INVENTION

The present invention is directed to trichothecene compositions and methods of inhibiting nematode infection of plants.

In a method of the present invention, a nematostatic amount of a trichothecene is applied to a plant and/or to the soil surrounding a plant in an amount that is effective to inhibit nematode infection. The amount of trichothecene administered is sufficient to prevent nematode infection, without toxic effect to the plant. Preferred concentrations of trichothecene for use in the present method are about 1 to about 1,000 parts per million (ppm), and more preferably about 500 ppm.

The method of the present invention is further directed to the application of a trichothecene composition in which the trichothecene is dissolved or dispersed in an appropriate carrier containing about 10 to about 20 volume percent of a nonionic surfactant, such as polyoxyethylenesorbitan monolaureate (commercially available as Tween® 80, Sigma Chemical Co., St. Louis, MO).

DESCRIPTION OF PREFERRED EMBODIMENTS

The present invention relates to trichothecene compositions and methods for inhibiting nematode infection of plants by providing a nematostatic amount of a trichothecene for application to the plant or to the soil surrounding the plant. As used herein, the phrases "prevent plant damage" and "control of growth" with respect to nematodes mean repels, prevents, reduces or eliminates multiplication or reproduction, growth, hatching or the existence of nematodes or nematode eggs.

Nematodes are parasitic worms that feed mostly on the roots of plants causing injury to the plants. Exemplary nematodes include *Meloidogyne incognita, Caenorhabditis elegans, Panagrellus redivivus, Turbatrix aceti* and *Aphelenchus avenae*.

As used herein, the term "nematocidal" refers to the killing of nematodes.

As used herein, the term "nematostatic" refers to the inhibition of nematode infection. A nematostatic agent inhibits the ability of nematodes to infect plants without directly killing the nematodes.

A nematocidal or a nematostatic composition of the present invention contains the active ingredient dissolved or dispersed in a carrier for administration. As used herein, a "carrier" is a material useful for administering the active ingredient to plants or to the soil surrounding plants and must be physiologically tolerable in the sense of being compatible with the other ingredients of the composition and not deleterious to plants.

The methods of using the nematocidal and/or nematostatic compositions of the present invention comprise applying a trichothecene together with a carrier to any field, fruit, vegetable, floral or ornamental crop or nursery crop that is sensitive to attack by plant parasitic nematodes, particularly the Meloidogyne species. Methods of application include direct application to the soil, controlled release of the composition in the surrounding soil, application to the plant roots directly before planting in the soil, foliar application and the like.

The term "soil," as used herein, is intended to include all media capable of supporting the growth of plants and may include humus, sand, manure, compost and the like.

In the present invention, a sub-phytotoxic amount of a trichothecene is applied in a nematostatic method to inhibit nematode infection of plants.

In a method of the present invention, a trichothecene is applied to a plant, and preferably by application to the soil surrounding the roots of the plant, in an amount which is sufficient to produce a nematostatic effect.

In a preferred embodiment, a composition containing about 500 ppm of a trichothecene together with a carrier is applied to the soil surrounding a plant in the method of the present invention. In a particularly preferred embodiment, roridin A is applied to a plant at a concentration of about 1 to about 1,000 ug/ml, and more preferably at a concentration of about 7.5 ug/ml. In another preferred embodiment of the present invention, a trichothecene dissolved or dispersed in an aqueous solution containing about 10 to about 20 volume percent of a nonionic surfactant is applied in the method of the present invention.

The trichothecenes of this invention can be used to control nematodes for a variety of agricultural applications on many different plants and fruits including, but not limited to, tomatoes, artichokes, aubergines, bananas, barley, beetroots, cacao, carrots, cassava, celery, chickpea, citrus, coconuts, coffee, corn, cotton, cowpeas, eggplants, field beans, forages, grapes, guava, melons, millet, oats, okra, ornamentals, papaya, peanuts, peppers, pigeon pea, pineapples, potatoes, rice, rye, sorghum, soybeans, sugar beets, sugar cane, sweet peppers, sweet potatoes, tea, tobacco, various lettuces, wheat and yams. Cultivated flowers can be protected according to the present invention, such as carnations, rose bushes, gerberas and chrysanthemums, pot plants, philodendrons, figs, pothos, sansevierias, and cacti; examples of nursery plants would include all the ornamental and flowering shrubs.

The trichothecenes can be incorporated into the soil of flowerpots or containers, by direct application to the area to be treated at the time of planting, or several days earlier, or by application of the compounds in a controlled-release form. Application can be by granule dispersement on the surface with turnover of the soil by a claw cultivator or a light plow, generally to about 10 cm to 20 cm depth of soil. The effective dose of the compounds will depend upon the population of the nematode expected to be encountered, the nematode type, soil, crop, and moisture, etc., and will range from about 10 grams to 100 pounds per acre.

For preparation of agricultural compositions from the trichothecenes of this invention, inert agriculturally acceptable carriers can be utilized which are either solid or liquid. Solid-form preparations include, but are not limited to, finely dispersible powders, dispersible granules and the like. Liquid-form preparations such as solutions, emulsions, suspensions, concentrates, emulsifiable concentrates, slurries and the like, may be used depending upon the application intended and the formulation media desired.

The trichothecenes of this invention may also be formulated as an active composition which may include finely divided dry or liquid diluents, extenders, fillers, conditioners and excipients, including various clays, diatomaceous earth, talc and the like, or water and various organic liquids and mixtures thereof. For those trichothecenes that are water-soluble, a drip irrigation method is also possible.

It is also contemplated that the compounds of this invention may be used in combination with other essential biologicals or beneficial microorganisms or active ingredients, such as herbicides, antimicrobials, fungicides, insecticides, plant growth regulators or nutrients.

The present invention is further illustrated by the following Examples which are not intended to limit the scope of the invention in any way.

EXAMPLE 1

To determine some of the properties and activity of the trichothecenes, contact assays were utilized. See Balan et al. (1974), Production of Nematode-Attracting and Nematocidal Substances by Predacious Fungi, Folia Microbiol, 19, 512–519.

The contact assay procedure utilized 100 microliters (ul) of a trichothecene compound in sterile water. All of the chemicals utilized were obtained from Sigma Chemical Co., St. Louis, MO. The contact assay was carried out in 96-well tissue culture plates.

The compounds tested were HT-2 toxin (15-acetoxy-3,4-dihydroxy-8-[3-methylbutyryloxy]-12,13-epoxytrichothec-9-ene), T-2 toxin (4,15-diacetoxy-3-hydroxy-8-[3-methylbutyryloxyl]-12,13-epoxytrichothec-9ene), diacetoxyscirpenol (4,15-diacetoxy-3-hydroxy-12,13-epoxytrichothec-9-ene), verrucarin A (muconomycin A), verrucarol (4,15-dihydroxy-12,13-epoxy-trichothec-9ene) and roridin A. The nematode species tested include the root-knot nematode (*Meloidogyne incognita* (Mi), the vinegar eelworm, *Turbatrix aceti* (Ta) formerly known as *Anquillula aceti*), *Caenorhabditis elegans* (Ce), *Panagrellus redivivus* (Pr) and *Aphelenchus avenae* (Aa). Each of the chemicals (2 mg) was suspended or dissolved in 4 ml of sterile deionized water, mixed thoroughly and used as the test material. Fifty to 100 nematodes were incubated in 100 ul of the test solution placed in each well of a 96-well microtiter plate. The plates were incubated at room temperature and observations on nematode motility were recorded at 24 and 48 hours. The treatments were replicated thrice. The results, shown in TABLE 1, show that trichothecenes do not have nematocidal activity.

TABLE 1

| EFFECT OF TRICHOTHECENES ON NEMATODE SPECIES | | | | | |
|---|---|---|---|---|---|
| | Nematode Species | | | | |
| TEST MATERIAL | Mi | Ce | Pr | Ta | Aa |
| HT-2 Toxin | − | − | − | − | − |
| T-2 Toxin | − | − | − | − | − |
| Diacetoxyscirpenol | − | − | − | − | − |
| Verrucarin A | − | − | − | − | − |
| Verrucarol | − | − | − | − | − |
| Roridin A | − | − | − | − | − |

TABLE 1-continued

| EFFECT OF TRICHOTHECENES ON NEMATODE SPECIES | | | | | |
|---|---|---|---|---|---|
| | Nematode Species | | | | |
| TEST MATERIAL | Mi | Ce | Pr | Ta | Aa |
| Water | − | − | − | − | − |

+ indicates death of nematodes and hence active compound
− indicates active nematodes and hence inactive compound + indicates death of nematodes and hence active compound − indicates active nematodes and hence inactive compound

EXAMPLE 2

The seed pouch assay method as known in the art is generically described in Preiser et al. (1981), A Soil-Free System for Assaying Nematocidal Activity of Chemicals, Nematology, 13, 535–537.

As used in this invention, the seed pouch assay is conducted by 1) placing two cucumber seeds (cultivar Straight Eight) into sterilized seed pouches. The pouches are maintained under high humidity conditions and moderate light intensity in a growth chamber. Approximately 5 to 6 days later, when the roots are 4 to 5 inches in length, the pouches are considered to be ready for use in the actual assay procedure; 2) prior to assaying, the trichothecene composition is prepared (2 mg per 4 ml of sterile water); and 3) 2 ml of the test material is pipetted around the root of each seedling. Twenty-four hours later, 2 ml of the suspension of nematodes containing approximately 2,000 freshly-collected, infective, second-stage juveniles of root-knot nematodes, *Meloidogyne incognita* was added to each pouch. Four to six pouches are maintained for each treatment and the remaining pouches are treated with water to serve as controls. The pouches are maintained in the growth chamber and observed for symptoms of nematode infection (root galling) after 10 to 14 days. In the case of TABLE 2, the nematodes were added 24 hours after application of the trichothecenes and the readings were taken 7 and 14 days after treatment. The results are as illustrated in TABLE 2 and establish that trichothecenes are nematostatic.

TABLE 2

| CONTROL OF NEMATODE INFECTION OF PLANTS BY TRICHOTHECENES | | |
|---|---|---|
| | # Galls/Seedling | |
| Test Material | 7 DAI* | 14 DAI |
| HT-2 Toxin | 0 | 0 |
| T-2 Toxin | 0 | 0 |
| Diacetoxyscirpenol | 0 | 0 |
| Roridin A | 2.2 | 3.3 |
| Verrucarin A | 1.5 | 24 |
| Verrucarol | 24.3 | 36.3 |
| Water | 17.1 | 37 |

*DAI - Days after inoculation

EXAMPLE 3

A cucumber seed pouch assay as described in Example 2 was carried out utilizing trichothecene compounds solubilized in an aqueous solution containing 19% by weight Tween ® 80. The incorporation of a nonionic surfactant into the composition increases trichothecene solubility by about 10- to about 60-fold.

The results are shown in TABLE 3 and confirm the nematostatic properties of the trichothecenes.

TABLE 3

NEMATODE CONTROL BY TRICHOTHECENES - SEED POUCH ASSAY

| Test Material and Conc. (ug/ml) | # Galls/Seedling | |
|---|---|---|
| | 7 DAI | 14 DAI |
| HT-2 Toxin | | |
| 250 | 0 | 0 |
| 125 | 0 | 0 |
| 62.5 | 0.5 | 3.0 |
| 31.3 | 1.5 | 7.5 |
| 15.6 | 7.0 | 20.5 |
| 7.8 | 15.5 | 29.5 |
| T-2 Toxin | | |
| 250 | 0 | 0 |
| 125 | 0 | 0 |
| 62.5 | 0 | 0 |
| 31.3 | 0 | 1.5 |
| 15.6 | 0 | 2.5 |
| 7.8 | 5.5 | 17.5 |
| Verrucarol | | |
| 500 | 7.5 | 7.5 |
| 250 | 25 | 36 |
| Diacetoxyscirpenol | | |
| 250 | 0 | 0 |
| 125 | 0 | 1.5 |
| 62.5 | 0 | 0 |
| 31.3 | 1 | 1 |
| 15.6 | 0 | 4 |
| Roridin A | | |
| 250 | 0 | 0 |
| 125 | 0 | 0 |
| 50 | 0 | 0.5 |
| 30 | 7 | 4.0 |
| 10 | 22 | 25 |
| 5 | 29 | 31 |
| Verrucarin A | | |
| 250 | 0 | 0 |
| 125 | 0 | 1 |
| 50 | 1 | 3 |
| 30 | 6 | 11 |
| 10 | 12 | 15 |
| 5 | 35 | 50 |
| Tween ® 80 (19%) | 31 | 48 |
| Untreated Control | 27.6 | 53 |

EXAMPLE 4

The pot test method known in the art is generically described in Di Sanzo et al. (1973), Nematode Response to Carbofuran, Nematology, 5, 22–27.

With greenhouse pot tests, 4-week-old tomato seedlings transplanted into 5-inch pots in sand are used. Roridin A (5 ml at 500 ppm suspensions) is pipetted around the root zone of the tomato seedlings. Twenty-four hours later, infective root-knot nematode juveniles (second-stage juveniles hatched from eggs approximately 5,000/plant) are added to each pot.

After 30 days, the plants are harvested and the roots observed for symptoms of nematode infection (galling). The results are shown in TABLE 4 and show that trichothecenes are effective nematostatic agents that do not negatively effect the plant (i.e., shoot and root weights).

TABLE 4

NEMATODE CONTROL BY RORIDIN A

| Treatment | Shoot wt. (gm) | Root wt. (gm) | # Galls/ gm root |
|---|---|---|---|
| Untreated Control | 31.9 | 7.95 | 0 |
| Inoculated Control | 32.9 | 10.1 | 45.7 |
| Roridin A (500 ppm) | 34.0 | 9.88 | 3.3 |

Numbers are average of four replicates.

EXAMPLE 5

An aqueous solution of roridin A containing 19% Tween ® 80 was prepared. The concentration of roridin A in this solution, as previously determined by HPLC, was 0.750 mg/ml. This was used as the stock solution and various dilutions (0.375, 0.19, 0.095, 0.0475 and 0.024 mg/ml) were prepared by serial dilution with water.

Root-knot nematode juveniles, as described in Example 4, were obtained. 100 ul of a suspension of nematodes, containing approximately 1,000 nematodes, was added to 1 ml of the stock solution contained in a 24-well microtiter plate. The tray was incubated overnight on a rotary shaker. Another batch of nematodes incubated in 19% Tween ® 80 solution was used as a control. After incubation, the nematodes were examined for motility, using a dissecting microscope. They were then concentrated by centrifugation (10,500 rpm for 1 minute) in a micro-centrifuge. The supernatant was removed and kept aside (W1). 1 ml of a 19% Tween ® 80 solution was added to the same tube, vortexed gently and centrifuged again. This step was repeated three times (W2–W4). The washed nematode pellet was suspended in 6 ml of water which was used to inoculate three seed pouches containing two plants each. The seed pouch assay was carried out as described in Example 3 using the treated nematodes, untreated nematodes and the wash solutions. In the case of wash solutions, the pouch assay was replicated only twice.

The results are shown in TABLE 5.

TABLE 5

EFFECT OF RORIDIN A ON NEMATODE INFECTIVITY

| Treatment | # Galls/Seedling | |
|---|---|---|
| | 7 DAYS* | 14 DAYS |
| Roridin A (0.75 mg/ml) | 0 | 0 |
| Roridin A (0.38 mg/ml) | 0 | 0 |
| Roridin A (0.19 mg/ml) | 0 | 0 |
| Roridin A (0.095 mg/ml) | 0 | 0 |
| Roridin A (0.047 mg/ml) | 0 | 0 |
| Roridin A (0.024 mg/ml) | 0 | 0 |
| Tween ® 80 (19% in water) | 26 | 36 |
| Tween ® 80 (9.5% in water) | 26 | 47 |
| Control (inoculated) | 25 | 31 |
| W1 | 0 | 0 |
| W2 | 1 | 1 |
| W3 | 11 | 15 |
| W4 | 15 | 26 |

*Numbers are average of four plants, except in the case of W1-W4.

*Numbers are average of four plants, except in the case of W1-W4.

The data show that pre-incubation in solutions of roridin A affects subsequent infectivity of root-knot nematode juveniles. No differences in the motility of infective juveniles was apparent.

The chemicals did not affect nematode movement as observed under a microscope. The motility of the treated nematodes was comparable to untreated controls.

In summary, the data obtained show trichothecenes to be effective nematostatic agents which are not toxic to plants.

The foregoing description and the Examples are intended as illustrative and are not to be taken as limiting. Still other variations within the spirit and scope of this invention are possible and will readily present themselves to those skilled in the art.

We claim:

1. A method for inhibiting nematode infection of plants without having a toxic effect to said plants, comprising:
applying to said plant, or to the soil surrounding said plant, a nematostatic effective amount of a trichothecene to produce a nematostatic effect in said plant.

2. The method of claim 1 wherein said trichothecene is selected from the group consisting of HT-2 toxin, T-2 toxin, trichoverroids, verrucarol, acetyl T-2 toxin, T-2 tetraol, diacetoxyscirpenol, neosolaniol, trichothecin, nivalenol and diacetylnivalenol.

3. The method of claim 1 wherein said trichothecene is selected from the group consisting of verrucarin A, roridin A and crotocin.

4. The method of claim 1 wherein said trichothecene is applied at a concentration of about 1 to about 1,000 ppm.

5. The method of claim 3 wherein said trichothecene is roridin A, said roridin A being applied at a concentration of about 1 to about 1,000 micrograms/ml.

6. The method of claim 5 wherein said roridin A concentration is about 7.5 micrograms/ml.

7. A method for inhibiting nematode infection of plants, comprising applying about 1 to about 10 ppm of Roridin A to a plant, or about 1 to about 1,000 ppm of Roridin A to the soil surrounding said plant, to produce a rematostatic effect in said plant without toxic effec to said plant.

* * * * *

UNITED STATES PATENT AND TRADEMARK OFFICE
CERTIFICATE OF CORRECTION

PATENT NO. : 5,030,450
DATED : July 9, 1991
INVENTOR(S) : Premachandran Devidas, Ronald R. Rasmussen It is certified that error appears in the above-identified patent and that said Letters Patent is hereby corrected as shown below:

Column 10, Line 13

"rematostatic" should read --nematostatic--

"effec" should read --effect--

Signed and Sealed this

Second Day of March, 1993

*Attest:*

STEPHEN G. KUNIN

*Attesting Officer*      Acting Commissioner of Patents and Trademarks